(12) United States Patent
Suen et al.

(10) Patent No.: US 7,271,268 B1
(45) Date of Patent: Sep. 18, 2007

(54) PROCESS FOR PREPARATION OF [1-(MERCAPTOMETHYL)CYCLOPROPYL] ACETIC ACID AND RELATED DERIVATIVES

(75) Inventors: Rung-Tian Suen, Taoyuan (TW); Yu-Liang Liu, Taoyuan (TW); Ching-Peng Wei, Taoyuan (TW)

(73) Assignee: Formosa Laboratories Inc., Taoyuan (TW)

( * ) Notice: Subject to any disclaimer, the term of this patent is extended or adjusted under 35 U.S.C. 154(b) by 0 days.

(21) Appl. No.: 11/615,779

(22) Filed: Dec. 22, 2006

(51) Int. Cl.
*C07D 413/00* (2006.01)
*C07C 61/04* (2006.01)
(52) U.S. Cl. ...................... 548/239; 562/506
(58) Field of Classification Search ..................... None
See application file for complete search history.

(56) References Cited

U.S. PATENT DOCUMENTS 5,270,324 A 12/1993 Zamboni et al.
5,523,477 A 6/1996 King et al.
5,534,651 A 7/1996 Quittmann et al.
6,512,140 B1 1/2003 Liu et al.

FOREIGN PATENT DOCUMENTS

| EP | 0480717 | 4/1992 |
| EP | 0604114 | 6/1994 |
| WO | 9518107 | 7/1995 |
| WO | 9622987 | 8/1996 |

OTHER PUBLICATIONS

Bioorganic & Medicinal Chemistry Letters, vol. 5, Issue 3, Feb. 2, 1995, pp. 283-288 M. Labelle, M. Belley, Y. Gareau, J. Y. Gareau, J. Y. Gauthier, D. Guay, R. Gordon, S. G. Grossman, T. R. Jones, Y. Leblanc, M. McAuliffe et al.

*Primary Examiner*—Paul A Zucker
(74) *Attorney, Agent, or Firm*—WPAT, P.C.; Anthony King

(57) ABSTRACT

The present invention provides a novel process for preparing [1-(mercaptomethyl)cyclopropyl]acetic acid with high purity and related derivatives.

28 Claims, 1 Drawing Sheet

Synthesis of [1-(Mercaptomethyl)cyclopropyl]acetic acid and related derivatives

PROCESS FOR PREPARATION OF [1-(MERCAPTOMETHYL)CYCLOPROPYL] ACETIC ACID AND RELATED DERIVATIVES

FIELD OF THE INVENTION

The present invention relates to a process for the preparation of [1-(mercaptomethyl)cyclopropyl]acetic acid and related derivatives.

BACKGROUND OF THE INVENTION

The compound [1-(mercaptomethyl)cyclopropyl]acetic acid and its derivatives are important intermediates for the synthesis of leukotriene receptor antagonist that inhibits are the cysteiny leukotriene CysL $T_1$ receptor. Leukotriene is associated with the inflammation and constriction of airway muscles and the accumulation of fluid in the lung. A number of leukotriene antagonists are described in EP 480,717 and EP 604,114, and U.S. Pat. No. 5,270,324. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

Among the compounds disclosed in these patents are those which include a thiomethylcyclopropaneacetic acid moiety. This moiety is introduced using derivatives of [1-(mercaptomethyl)cyclopropyl]acetic acid. A number of methods for preparing [1-(mercaptomethyl)cyclopropyl] acetic acid are known, Most known syntheses for preparing [1-(mercaptomethyl)cyclopropyl]acetic acid use either thiolacetic acid or hydrogen sulfide derivatives to introduce the mercapto function. EP 480,717 discloses the [1-(mercaptomethyl)cyclopropyl]acetic acid is introduced using methyl [1-(mercaptomethyl)cyclopropyl]acetate, and the methyl [1-(mercaptomethyl) cyclopropyl]acetate is prepared from 1,1-cyclopropyldimethanol. An improved synthesis is used in U.S. Pat. No. 5,270,324 and EP 604,114, which involves first converting 1,1-cyclopropyldimethanol into the corresponding cyclic sulfite using thionyl chloride.

Subsequently, it has been discovered that [1-(mercaptomethyl)cyclopropyl]acetic acid can be prepared from [1-(acetylthiolmethyl)cyclopropyl]acetonitrile by conducting the basic hydrolysis in a biphasic system, the product may then be crystallized from a hydrocarbon such as hexane or heptane. In the previous process for preparing [1-(mercaptomethyl)cyclopropyl]acetic acid, the method for preparing cyclic sulfite results in a number of by-products thereby reducing the yield of the desired cyclic sulfite; the process also requires multiple aqueous extractions, and solvent switches rendering it difficult to adapt to large scale production. Alternative processes are disclosed in the literature (Bioorg Med Chem Lett., 5, 1995) and in WO 95/18107, WO 96/22987, and U.S. Pat. No. 5,523,477 and U.S. Pat. No. 5,534,651.

Due to the strong disagreeable odour used in prior art, the manipulation of these reagents and the corresponding synthetic intermediates is technically demanding. Further, essentially all the key intermediates in known syntheses are liquids or oils, which require either vacuum distillation or column chromatography for purification. In addition, the final step of each of known syntheses involves a hot basic hydrolysis in which the temperature ranges from 80° C. to aqueous reflux. Since [1-(mercaptomethyl)cyclopropyl]acetic acid is sensitive to oxidation, the use of such harsh reaction conditions leads to reduced yields and/or product of unacceptable purity. U.S. Pat. No. 6,512,140 disclosed a novel process for the preparation of [1-(mercaptomethyl) cyclopropyl]acetic acid which avoids the above-described disadvantages of known processes. However, it may have the corresponding disulfide of the final products, and the reaction temperature lower to 0° C. is inconvenient with respect to industrial application.

SUMMARY OF THE INVENTION

The present invention is related to a novel and efficient process for the preparation of [1-(mercaptomethyl)cyclopropyl]acetic acid with high purity and related derivatives with respect to industrial application.

In one aspect, the present invention provides a process for preparing [1-(mercaptomethyl)cyclopropyl]acetic acid of the following formula

by converting a compound of the following formula

wherein R represents alkyl and cycloalkyl, with a base in a solvent of an alcohol.

In another aspect, the present invention provides a process for preparing {1-[4,4-dimethyl-4,5-dihydro-1,3-oxazo-2-yl] methyl}cyclopropyl}methanethiol of the following formula

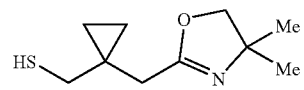

comprising the steps of: (a) reacting a compound selected from the group consisting of [1-(mercaptomethyl)cyclopropyl]acetic acid and/or methyl [1-(mercaptomethyl)cyclopropyl]acetate with an amino alcohol in the presence of a catalyst in an organic solvent capable of azotropic removal of water and/or methanol to form a mixture; and (b) heating the mixture from the step (a).

DETAILED DESCRIPTION OF THE INVENTION

Figure 1:
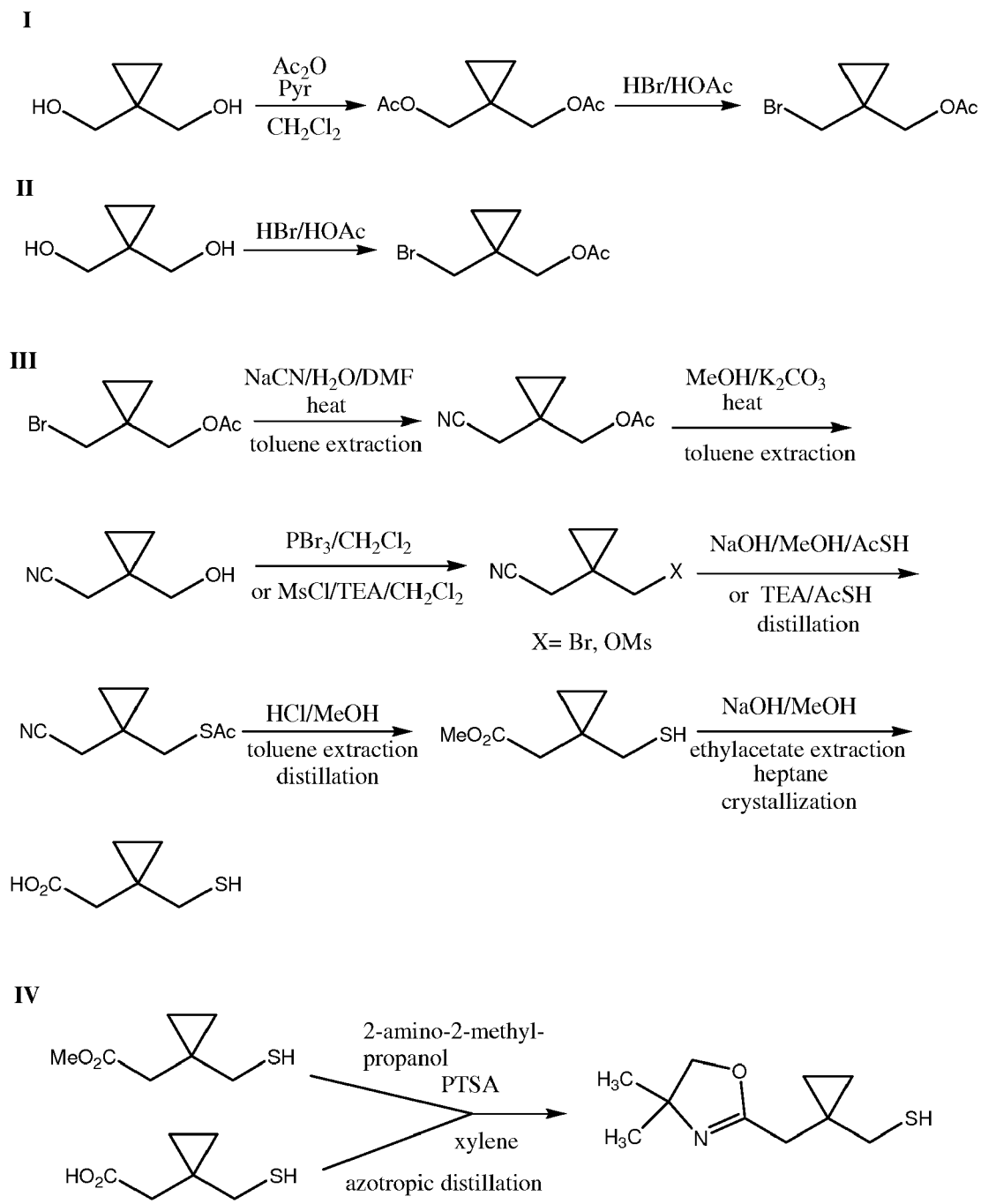
FIG. 1 shows the preparation of the present invention.

The present invention provides a novel process for the preparation of [1-(mercaptomethyl)cyclopropyl]acetic acid with high purity and related derivatives. The present invention provides an efficient method with improved yield and purity for use in industrial application.

Accordingly, the present invention provides a process for preparing [1-(mercaptomethyl)cyclopropyl]acetic acid of the following formula

by converting a compound of the following formula

wherein R represents alkyl and cycloalkyl, preferably represents $C_{1-10}$ alkyl and $C_{3-10}$ cycloalkyl, more preferably represents $C_{1-4}$ alkyl, most preferably represents methyl, with a base in a solvent of an alcohol. The reaction is carried out at a temperature ranging from about 30° C. to about 99° C., preferably from about 40° C. to 90° C., more preferably from about 50° C. to about 85° C., most preferably from about 60° C. to 80° C. The reaction was aged for a period of about 1~2 hours until completion of reaction. When the reaction is complete, the temperature was lowered below 40° C. The resulting solution was acidified to pH=3.0~4.0 with HCl aqueous solution. After the reaction mixture was filtered, the resulting mixture was purified by extraction with alkyl acetate and crystallization from an organic solvent.

In the present invention, the base is selected from the group consisting of sodium hydroxide, sodium carbonate, sodium bicarbonate, potassium carbonate, potassium bicarbonate, and potassium hydroxide. A particularly preferred base is sodium hydroxide. In addition, preferred alcohol for use in the reaction is $C_{1-4}$ alcohol. In the preferred embodiment, the $C_{1-4}$ alcohol is methanol.

In the present invention, the alkyl acetate is selected from the group consisting of methyl acetate, ethyl acetate, propylacetate, isopropylacetate, butyl acetate, sec-butyl acetate, and tert-butyl acetate. In the preferred embodiment, the extraction is made by ethylacetate. In addition, the crystallization is carried out using an organic solvent selected from the group consisting of toluene, hexane, and heptane. Preferably, the crystallization is made from heptane for about 4 to 5 hrs with the reaction temperature about 0° C. to 10° C., more preferably about 10° C.

In the present invention, the compound of the following formula

is prepared by converting [1-(acetylthiomethyl) cyclopropyl]acetonitrile of the following formula

with an acid and a alcohol. The reaction solution was heated to reflux and was aged for a period of about 20 hours. When the reaction was complete, the reaction mixture was further extracted by toluene.

In the preferred embodiment, the acid is organic acid or mineral acid, more preferably is hydrogen chloride. Preferred alcohol for the reaction is $C_{1-4}$ alcohol, more preferably is methanol.

In the process of the present invention, the [1-(acetylthiolmethyl)cyclopropyl]acetonitril is prepared by converting [1-(bromomethyl) cyclopropyl]acetonitrile of the following formula

with thiolacetic acid in the presence of sodium hydroxide or potassium carbonate in an organic solvent of methanol or DMF.

In the process of the present invention, the [1-(acetylthiolmethyl)cyclopropyl]acetonitrile is prepared by converting [1-(cyanomethyl)cyclopropyl]methyl methanesulfonate of the following formula

with thiolacetic acid in the presence of triethylamine.

In the process of the present invention, the [1-(bromomethyl)cyclopropyl]acetonitrile is prepared by converting [1-(hydroxymethyl)cyclopropyl]acetonitrile of the following formula

with phosphorus tribromide in an organic solvent of methylene chloride.

In the process of the present invention, the [1-(cyanomethyl)cyclopropyl]methyl methanesulfonate is prepared by converting [1-(hydroxymethyl) cyclopropyl]acetonitrile with methenesulfonyl chloride in the presence of triethylamine in an organic solvent of methylene chloride or toluene.

In the process of the present invention, the [1-(hydroxymethyl) cyclopropyl]acetonitrile is prepared by converting [1-(cyanomethyl) cyclopropyl]methyl acetate of the following formula

with potassium carbonate in an organic solvent of methanol.

In the process of the present invention, the [1-(cyanomethyl)cyclopropyl]methyl acetate is prepared by converting [1-(bromomethyl)cyclopropyl]methyl acetate of the following formula

with sodium/potassium cyanide in an organic solvent of N,N-dimethylformamide or dimthylsulfoxide.

In the process of the present invention, the [1-(bromomethyl)cyclopropyl]methyl acetate is prepared by converting 1,1-cyclopropyldimethanol of the following formula

with hydrogen bromide and glacial acetic acid in an organic solvent of methylene chloride.

In the process of the present invention, the [1-(bromomethyl)cyclopropyl]methyl acetate is prepared from 1,1-cyclopropyldimethanol comprising the steps of:
(a) reacting 1,1-cyclopropyldimethanol acetic anhydride in the presence of pyridine in an organic solvent of methylene chloride to provide cyclopropane-1,1-diylbis(methylene) diacetate of the following formula;

and
(b) reacting cyclopropane-1,1-diylbis(methylene) diacetate with HBr and glacial acetic acid.

The present invention further provides a process for preparing {1-[4,4-dimethyl-4,5-dihydro-1,3-oxazo-2-yl]methyl} cyclopropyl}methanethiol of the following formula

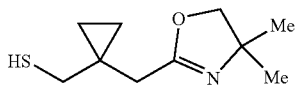

comprising the steps of:
(a) reacting a compound selected from the group consisting of [1-(mercaptomethyl) cyclopropyl]acetic acid and methyl [1-(mercaptomethyl)cyclopropyl]acetate with an amino alcohol in the presence of a catalyst in an organic solvent capable of azotropic removal of water and/or methanol to form a mixture; and
(b) heating the mixture from the step (a) to about 120° C. to 200° C.

In the preferred embodiment, the amino alcohol is 2-amino-2-methyl-1-propanol.

In the process of the present invention, the catalyst is acid. In the preferred embodiment, the acid is organic acid or mineral acid, more preferably is p-toluenesulfonic acid.

In the process of the present invention, the organic solvent is selected from the group consisting of toluene, xylene and benzene, or a mixture of solvents selected from the group consisting of toluene, xylene and benzene. In the preferred embodiment, the organic solvent is benzene, more preferably is xylene.

In the preferred embodiment, the mixture from the step (a) is heated to about 120° C. to 150° C.

EXAMPLE

The examples below are non-limited and are merely representative of various aspects and features of the present invention.

Example 1

Preparation of [1-(bromomethyl)cyclopropyl]methyl acetate

A 3 L 3-neck round bottle flask was equipped with mechanical stirrer, a thermometer, a nitrogen inlet and an additional funnel. To the flask was charged 200 g of 1,1-cyclopropyldimethanol and 200 mL of methylene chloride. The mixture was cooled to 0~5° C. 1440 g of 33% HBr in glacial acetic acid was slowly added to reaction solution and kept the temperature below 20° C. After the addition, the reaction mixture was stirred at between 10° C. and 18° C. for about 2 hours and then warmed to 16~22° C. and stirred about 1 hour. When the starting material of 1,1-cyclopropyldimethanol was disappeared (checked by TLC, mobile phase:EA/hx=1/3(V/V)), 1000 mL of water was added to the reaction mixture with stirring over 30 min and kept the temperature below 20° C. The layers were separated and the aqueous layer was back extracted with 300 mL methylene chloride. To the combined organic layers was added 400 ml of water, and then was neutralized to pH 6~7 with 10% NaOH aqueous solution. The organic layers were concentrated to obtain 396 g of crude [1-(bromomethyl)cyclopropyl]methyl acetate.

Example 2

Preparation of cyclopropane-1,1-diylbis(methylene) diacetate

A 50 mL 3-neck round bottle flask was equipped with condenser, an addition funnel and a thermometer. Charge 2 g of 1,1-cyclopropyldimethanol, 5 g of acetic anhydride, 2 mL of methylene chloride and 0.77 g of pyridine to the flask. The reaction mixture was heated to about 90~95° C. and kept continuous stirring about 1 hour. When the reaction was completed, the mixture was cooled and the 14.4 g of 33% HBr in glacial acetic acid was added while maintain below 20° C. After the addition, the reaction mixture was stirred about 6 hours and then 2 mL of methylene chloride and 10 mL of water was added into the flask. The layers were separated and the aqueous layer was extracted twice with 4 mL of methylene chloride. Combined the organic layers and washed twice with 6 mL of water and then neutralized to pH=8 with sodium carbonate solution. The organic layers were concentrated to obtain 3.3 g of crude [1-(bromomethyl) cyclopropyl]methyl acetate.

Example 3

Preparation of [1-(cyanomethyl)cyclopropyl]methyl acetate

A 12 L 4-neck round bottle flask was equipped with mechanical stirrer, a thermometer, a condenser, a nitrogen inlet and an additional funnel. To the flask was charged 1335 mL of and 667 g of potassium cyanide and kept stirring to complete dissolution. 1417 g of DMF and 1417 g of crude [1-(bromomethyl)cyclopropyl]methyl acetate were added from the addition funnel over 30 min. When the addition was complete, the reaction mixture was heated to 80° C. with stirring about 1 hour. The resulting mixture was cooled to about 20~25° C. 3500 mL of water and 3500 mL of toluene were added to the reaction mixture with stirring over 30 min. The layers were separated and the aqueous layer was back extracted with 3500 mL of toluene. Combined the organic layer and then concentrated to obtain 1253 g dark brown liquid.

Example 4

Preparation of [1-(hydroxymethyl)cyclopropyl]acetonitrile

A 12 L 4-neck round bottle flask was equipped with mechanical stirrer, a thermometer, a condenser, a nitrogen inlet and an additional funnel. To the 1253 g of dark brown liquid produced in Example 3 was added 1129 g of potassium carbonate and 3760 mL of methanol and the resulting mixture was heated to 50° C. and aged for a period of about 1 hour until completion of reaction as checked by TLC (mobile phase: EA/hx=1/2(V/V)). The reaction mixture was cooled to room temperature. After filtration with about 250 g of celite, cake was washed with 1360 mL of toluene. Combined the filtrate and washing solution and concentrated by rotary evaporator to obtain dark brown liquid with a little solid. The resulting mixture was filtered again with about 60 g of celite. The cake was washed with 1000 mL of methylene chloride. The resulting filtrate was concentrated to obtain 603 g of viscous dark brown liquid.

Example 5

Preparation of [1-(bromomethyl)cyclopropyl]acetonitrile

A 12 L 4-neck round bottle flask was equipped with mechanical stirrer, a thermometer, a condenser, a nitrogen inlet and an additional funnel. The system was linked to caustic scrubber. To the 603 g of dark brown liquid produced in Example 4 was added 1809 Of methylene chloride. The resulting solution was transferred to the addition funnel. 1500 g of phosphorus tribromide was charged to the flask and then was cooled to about 10° C. The above-mentioned dark brown liquid was slowly added to flask and kept the temperature below 10° C. during addition. After the addition, the resulting mixture was aged for a period of about 12 hours until completion of reaction as checked by TLC (mobile phase: EA/hx=1/3(V/V)). Transferred the reaction mixture into the ice-cold aqueous solution with vigorously stirring over 30 min and kept temperature below 20° C. The layers were separated and the organic layer was washed with 3600 mL of water and then was neutralized to pH=8 with 360 mL of 10% sodium bicarbonate aqueous solution. The resulting solution became pale yellowish turbid solution. After filtration and concentration of the solution, 382.8 g of dark red liquid was obtained.

Example 6

Preparation of [1-(cyanomethyl)cyclopropyl]methyl methanesulfonate

A 12 L 4-neck round bottle flask was equipped with mechanical stirrer, a thermometer, a condenser, a nitrogen inlet and an additional funnel. To the 603 g of dark brown liquid of [1-(hydroxymethyl)cyclopropyl]acetonitrile was added 2300 mL of toluene and 460 g of triethylamine. The reaction mixture was cooled to about 0~5° C. and then 414 g of methenesulfonyl chloride was slowly added to the reaction flask and kept the temperature below 5° C. during addition. After the addition, the resulting mixture was aged for a period of about 1 hours until completion of reaction as checked by GC or by TLC (mobile phase: EA/hx=1/1(V/V)). The produce did not isolate, it could be used directly to the following step.

Example 7

Preparation of [1-(acetylthiolmethyl)cyclopropyl]acetonitrile

A 3 L 4-neck round bottle flask was equipped with mechanical stirrer, a thermometer, a condenser, a nitrogen inlet and an additional funnel. To the 382.2 g of dark red liquid produced in Example 5 was added 304 g of potassium carbonate and 383.2 g of DMF. The reaction mixture was cooled to about 10° C., and then 156 mL of thiolacetic acid was slowly added into the solution in a period of about 2 hours. After the addition, the resulting resolution become yellow turbid and was aged for a period of about 1 hour until completion of reaction as check by TLC (mobile phase: EA/hx=1/3)). 1914 mL of ice-water and 1914 mL toluene was added to the reaction mixture was vigorous stirring. The layers was separated and the organic layer was concentrated by rotatory evaporator to obtain 420 g of brown liquid. Purified by simple distillation to afford 350 g of [1-(acetylthiolmethyl)cyclopropyl]acetonitrile (purity by GC: 85%)

Example 8

Preparation of [1-(acetylthiolmethyl)cyclopropyl]acetonitrile

A 3 L 4-neck round bottle flask was equipped with mechanical stirrer, a thermometer, a condenser, a nitrogen inlet and an additional funnel. To the resulting solution produced in Example 6 was added 400 g of triethylamine. 252 g of thiolacetic acid was slowly added into the reaction mixture while addition the temperature was controlled below 5° C. After the addition, the reaction mixture was stirred at between 0~5° C. about 1 hour and then warmed to 25~30° C. and stirred about 6~8 hours. GC was checked on a sample of the reaction conforming the disappearing of [1-(cyanomethyl)cyclopropyl]methyl methanesulfonate or TLC was checked on a sample of the reaction conforming the formation of [1-(acetylthiolmethyl)cyclopropyl]acetonitrile. The resulting solution was filtered and the cake was washed with 400 mL of toluene. To the filtrate was added 2000 mL of water with vigorous stirring over 30 min. The reaction mixture was filtered with 20 g of celite and cake was washed with 200 mL of toluene. The filtrate was stand for separation. The organic layer was washed with 2000 mL of water. The resulting organic solution was concentrated by rotatory evaporator and then purified by vacuum distillation to afford 450 g of [1-(acetylthiolmethyl)cyclopropyl]acetonitrile (purity by GC:87~88%).

Example 9

Preparation of methyl [1-(mercaptomethyl)cyclopropyl]acetate

A 5 L 4-neck round bottle flask was equipped with mechanical stirrer, a thermometer, a condenser, a nitrogen inlet and an additional funnel. Charge 2020 mL of methanol, 662 mL of 32% HCl aqueous solution and 420 g of [1-(acetylthiolmethyl)cyclopropyl]acetonitrile produced from Example 8 to the reaction flask. The reaction solution was heated to reflux at 70~75° C. The resulting solution was aged for a period of about 20 hours until completion of reaction as check by GC. When the reaction was complete, 1600 mL of toluene and 150 mL of water were added with vigorous stirring over 30 min. The layers were separated and aqueous layer was back extracted with 1600 mL of toluene. Combined the organic layers and then washed with 900 mL of brine. The organic layer was concentrated by rotatory evaporator to obtain 434 g of yellow clear solution of crude methyl [1-(mercaptomethyl)cyclopropyl]acetate. Purified by vacuum fractional distillation to obtain 280 g of colorless to pale yellow of methyl [1-(mercaptomethyl)cyclopropyl] acetate (purity by GC>85%) liquid. If thiolactone was combined, the purity (by GC) was more than 98%. $H^1$-NMR ($CDCl_3$): 0.51 ppm ($CH_2$, t), 0.55 ppm ($CH_2$, t), 1.33 ppm (SH, t), 2.44 ppm ($CH_2$,s), 257~2.61 ppm ($CH_2$, d), 3.67 ppm ($CH_3$, s)

Example 10

Preparation of [1-(mercaptomethyl)cyclopropyl]acetic acid

A 5 L 4-neck round bottle flask was equipped with mechanical stirrer, a thermometer, a condenser, a nitrogen inlet and an additional funnel. Prepare 47% of sodium hydroxide solution from 855 g of sodium hydroxide was dissolved in 972 mL of water. Charge 1800 g of [1-(mercaptomethyl)cyclopropyl]acetate, 1540 mL of methanol to the reaction flask. 1540 g of 47% sodium hydroxide aqueous solution was slowly added to the reaction mixture. After the addition, the reaction mixture was heated to 70~80° C. and was aged for a period of about 2 hours until completion of reaction as check by TLC (mobile phase: EA/hx=1/2(V/V)). When the reaction was complete, the temperature was lowered below 40° C. The resulting resolution was acidified to pH=3.0~4.0 with about 1800 mL of 32% HCl aqueous solution. After the reaction mixture was filtered, 2700 g of ethylacetate was added to the filtrate with vigorous stirring over 30 min. The layers were separated; cake and 1000 g of water were added to the aqueous layer and back extracted with 2700 g of ethylacetate. Combined the organic layers and concentrated by rotatory evaporator. Temperature was controlled at 3018 40° C. and pressure was controlled below 100 torr. Distillation was continued to collect about 4000~5000 mL of distillate. 2000 mL of heptanes was added and the distillation was continued to collect about 1000~2000 mL at 30~40° C./<100 torr. After the addition of 2100 g of heptanes, the reaction mixture was cooled to at 10° C. for about 4~5 hours. A large amount of white solid was obtained by filtration. Cake was washed with 1000 g of heptanes. 1468 g of pure [1-(mercaptomethyl)cyclopropyl]acetic acid was obtained by vacuum dried. (purity by GC: >99%, m.p.=42~45° C.), $H^1$-NMR ($CDCl_3$): 0.55 ppm ($CH_2$, t), 0.58 ppm ($CH_2$,t), 1.34 ppm (SH, t), 2.50 ppm ($CH_2$, s), 2.60 ppm ($CH_2$, d)

Example 11

Preparation of {1-[4,4-dimethyl-4,5-dihydro-1,3-oxazo-2-yl]methyl}cyclopropyl}methanethiol A 12 L 4-neck round bottle flask was equipped with mechanical stirrer, a thermometer, a condenser attached with Dean-Stark apparatus, a nitrogen inlet and an additional funnel. To the flask was charged 1800 g of [1-(mercaptomethyl)cyclopropyl]acetic acid, 1000 g of 2-amino-2-methyl-1-propanol, 3600 mL of xylene and 180 g of p-toluenesulfonic acid. The reaction mixture was heated to 120~130° C. and kept stirring about 2 hours. Water and 2-amino-2-methyl-1-propanol were collected by azotropic distillation under this condition. Another 1200 g of 2-amino-2-methyl-1-propanol was added into the reaction mixture by addition funnel. After the addition, the resulting solution was heated to 120~130° C. and was aged for a period of about 2 hours until completion of reaction as check by GC. The reaction temperature was raised to 140~150° C. for about 40 hours. When the reaction was complete, the reaction mixture was cooled to 80~90° C. 2700 mL of water was added to the flask with vigorous stirring over 30 min. The layers were separated and the organic layer was concentrated by rotatory evaporator. Purified by vacuum distillation at 115~125° C./12~18 torr to obtain 1750 g of colorless to pale yellow of Title compound (purity by GC: >95%)

Example 12

Preparation of {1-[4,4-dimethyl-4,5-dihydro-1,3-oxazo-2-yl]methyl}cyclopropyl}methanethiol A 12 L 4-neck round bottle flask was equipped with mechanical stirrer, a thermometer, a condenser attached with Dean-Stark apparatus, a nitrogen inlet and an additional funnel. To the flask was charged 2000 g of methyl [1-(mercaptomethyl)cyclopropyl]acetate. 1110 g of 2-amino-2-methyl-1-propanol, 4000 mL of xylene and 190 g of p-toluenesulfonic acid. The reaction mixture was heated to 120~130° C. and kept stirring about 2 hours. Methanol, water and 2-amino-2-methyl-1-propanol were collected by azotropic distillation under this condition. Another 1330 g of 2-amino-2-methyl-1-propanol was added into the reaction mixture by addition funnel. After the addition, the resulting solution was heated to 120~130° C. and was aged for a period of about 2 hours until completion of reaction as check by GC. The reaction temperature was raised to 140~150° C. for about 60 hours. When the reaction was complete, the reaction mixture was cooled to 80~90° C. 2700 mL of water was added to the flask with vigorous stirring over 30 min. The layers were separated and the organic layer was concentrated by rotatory evaporator. Purified by vacuum distillation at 115~125° C./12~18 torr to obtain 1860 g of colorless to pale yellow of Title compound (purity by GC: >95%). $H^1$-NMR($CDCl_3$): 0.49~0.51 ppm ($CH_2$, m), 0.56·0.63 ppm ($CH_2$, m), 1.24 ppm (2$CH_3$, s), 1.44 ppm (SH, t), 2.39 ppm ($CH_2$, s), 2.52~2.56 ppm ($CH_2$, d), 3.89 ppm ($CH_2$, s)

What is claimed is:

1. A process for preparing high purity [1-(mercaptomethyl)cyclopropyl]acetic acid of the following formula

by converting a compound of the following formula

wherein R represents alkyl and cycloalkyl, with a base in a solvent of an alcohol.

2. The process according to claim 1, wherein the base is selected from the group consisting of sodium hydroxide, sodium carbonate, sodium bicarbonate, potassium bicarbonate, potassium carbonate, and potassium hydroxide.

3. The process according to claim 2, wherein the base is sodium hydroxide.

4. The process according to claim 1, wherein the compound of the following formula

is prepared by converting [1-(acetylthiolmethyl) cyclopropyl]acetonitrile of the following formula

with an acid and an alcohol.

5. The process according to claim 4, wherein the acid is organic acid or mineral acid.

6. The process according to claim 5, wherein the acid is hydrogen chloride.

7. The process according to claim 1, wherein the alcohol is a $C_{1-4}$ alcohol.

8. The process according to claim 1, further comprising purification by extraction and crystallization.

9. The process according to claim 8, wherein the extraction is made by alkyl acetate.

10. The process according to claim 9, wherein the alkyl acetate is selected from the group consisting of methyl acetate, ethyl acetate, propylacetate, isopropylacetate, butyl acetate, sec-butyl acetate, and tert-butyl acetate.

11. The process according to claim 8, wherein the crystallization is from an organic solvent.

12. The process according to claim 11, wherein the organic solvent is selected from the group consisting of toluene, hexane, and heptane.

13. The process according to claim 1, wherein the reaction temperature is about 30° C. to about 80° C.

14. The process according to claim 4, further comprising extraction of methyl [1-(mercaptomethyl)cyclopropyl]acetate by an organic solvent.

15. The process according to claim 14, wherein the organic solvent is toluene.

16. The process according to claim 4, wherein the [1-(acetylthiolmethyl)cyclopropyl]acetonitrile is prepared by converting [1-(bromomethyl)cyclopropyl]acetonitrile of the following formula

with thiolacetic acid in the presence of sodium hydroxide or potassium carbonate in an organic solvent of methanol or N,N-dimethylformamide.

17. The process according to claim 4, wherein the [1-(acetylthiolmethyl)cyclopropyl]acetonitrile is prepared by converting [1-(cyanomethyl)cyclopropyl]methyl methanesulfonate of the following formula

with thiolacetic acid in the presence of triethylamine.

18. The process according to claim 16, wherein the [1-(bromomethyl)cyclopropyl]acetonitrile is prepared by converting [1-(hydroxymethyl)cyclopropyl]acetonitrile of the following formula

with phosphorus tribromide in an organic solvent of methylene chloride.

19. The process according to claim 17, wherein the [1-(cyanomethyl)cyclopropyl]methyl methanesulfonate is prepared by converting [1-(hydroxymethyl)cyclopropyl]acetonitrile with methenesulfonyl chloride in the presence of triethylamine in an organic solvent of methylene chloride or toluene.

20. The process according to claim 18, wherein the [1-(hydroxymethyl)cyclopropyl]acetonitrile is prepared by converting [1-(cyanomethyl)cyclopropyl]methyl acetate of the following formula

with potassium carbonate in an organic solvent of methanol.

21. The process according to claim 20, wherein the [1-(cyanomethyl)cyclopropyl]methyl acetate is prepared by converting [1-(bromomethyl)cyclopropyl]methyl acetate of the following formula

with sodium/potassium cyanide in an organic solvent of N,N-diemthylformamide or dimethylsulfoxide.

22. The process according to claim 21, wherein the [1-(bromomethyl)cyclopropyl]methyl acetate is prepared by converting 1,1-cyclopropyldimethanol of the following formula

with hydrogen bromide and glacial acetic acid in an organic solvent of methylene chloride.

23. The process according to claim 22, wherein the [1-(bromomethyl)cyclopropyl]methyl acetate is prepared from 1,1-cyclopropyldimethanol comprising the steps of:
(a) reacting 1,1-cyclopropyldimethanol acetic anhydride in the presence of pyridine in an organic solvent of methylene chloride to provide cyclopropane-1,1-diyl-bis(methylene) diacetate of the following formula;

and
(b) reacting cyclopropane-1,1-diylbis(methylene) diacetate with HBr and glacial acetic acid.

24. A process for preparing {1-[4,4-dimethyl-4,5-dihydro-1,3-oxazo-2-yl]methyl}cyclopropyl}methanethiol of the following formula

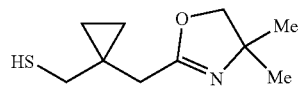

comprising the steps of:
(a) reacting a compound selected from the group consisting of [1-(mercaptomethyl)cyclopropyl]acetic acid and/or methyl [1-(mercaptomethyl)cyclopropyl]acetate with an amino alcohol in the presence of a catalyst in an organic solvent capable of azotropic removal of methanol and/or water for form a mixture; and
(b) heating the mixture from the step (a).

25. The process according to claim 24, wherein the amino alcohol is 2-amino-2-methyl-1-propanol.

26. The process according to claim 24, wherein the catalyst is organic acid or mineral acid.

27. The process according to claim 24, wherein the organic solvent is selected from the group consisting of toluene, xylene, and benzene, or a mixture of solvents selected from the group consisting of toluene, xylene, and benzene.

28. The process according to claim 24, wherein the temperature of the step (b) is about 120° C. to 200° C.

* * * * *